(12) United States Patent
Dennin et al.

(10) Patent No.: US 8,071,086 B2
(45) Date of Patent: Dec. 6, 2011

(54) BACTERIAL COMPOSITION AND ITS USE

(75) Inventors: Véronique Dennin, Villeneuve d'Ascq (FR); Gregory John Leyer, Madison, WI (US); Annick Mercenier, Epalinges (CH); Sophie Nutten, Steenvoorde (FR); Bruno Pot, St-Michiels Brugge (BE)

(73) Assignee: Danisco A/S, Copenhagen K (DK)

( * ) Notice: Subject to any disclaimer, the term of this patent is extended or adjusted under 35 U.S.C. 154(b) by 0 days.

(21) Appl. No.: 12/778,509

(22) Filed: May 12, 2010

(65) Prior Publication Data

US 2010/0322964 A1    Dec. 23, 2010

(51) Int. Cl.
*C12N 1/20* (2006.01)
*A01N 1/20* (2006.01)
*A61K 35/74* (2006.01)

(52) U.S. Cl. ............... 424/93.3; 424/93.4; 424/93.45

(58) Field of Classification Search ............... None
See application file for complete search history.

(56) References Cited

U.S. PATENT DOCUMENTS

| | | |
|---|---|---|
| 6,358,521 B1 | 3/2002 | Izvekova et al. |
| 6,419,926 B2 | 7/2002 | Kodama et al. |
| 7,195,906 B2 | 3/2007 | Collins et al. |
| 2002/0006432 A1 | 1/2002 | Collins et al. |

OTHER PUBLICATIONS

Foligne et al. "Correlation between in vitro and in vivo immunomodulatory properties of lactic acid bacteria" World Jour of Gastroenterology, Jan. 14, 2007 (13) 2 pp. 236-243.
Daniel et al. "Selecting Lactic Acid Bacterial for Their Safety and Functionality by Use of a Mouse Colitis Model" Applied and EnvironmentalMicrobio. Sep. 2006 pp. 5799-5805.

*Primary Examiner* — Herbert J. Lillng
(74) *Attorney, Agent, or Firm* — Fay Sharpe LLP

(57) ABSTRACT

The subject of the present invention is a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802. An other subject of the invention is an immunomodulation method comprising the step of using the at least one strain selected from the preceding group.

7 Claims, 3 Drawing Sheets

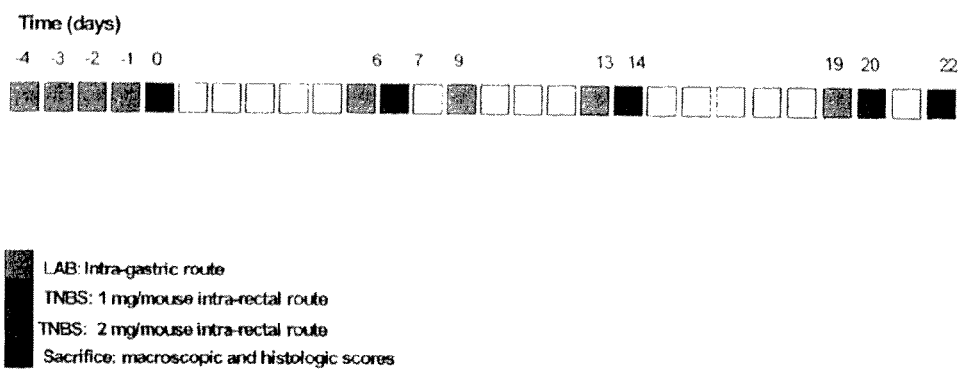
Figure 1: schedule of probiotic administration
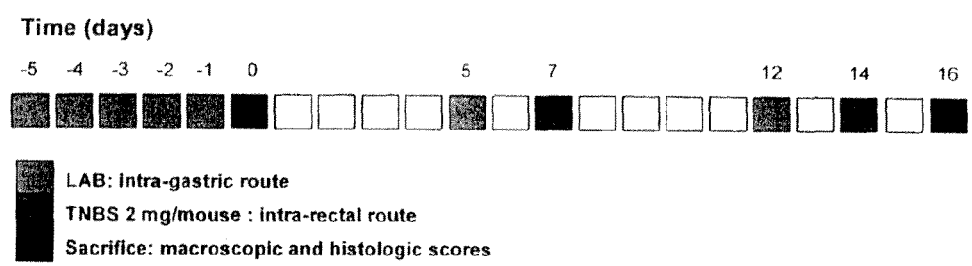
Figure 3: schedule of probiotic administration
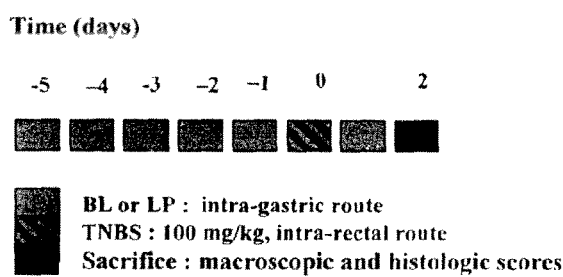
Figure 5: schedule of probiotic administration

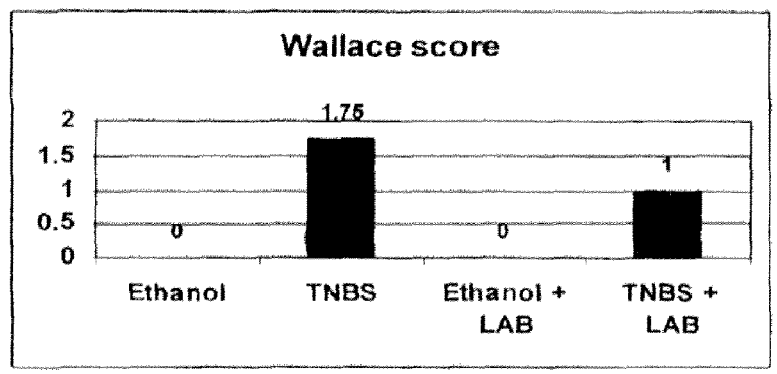
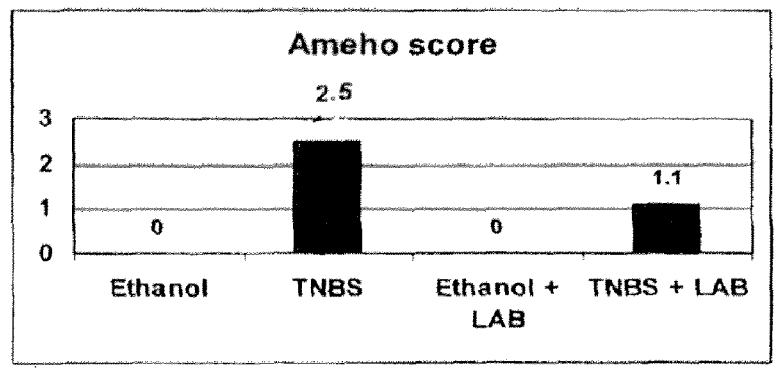
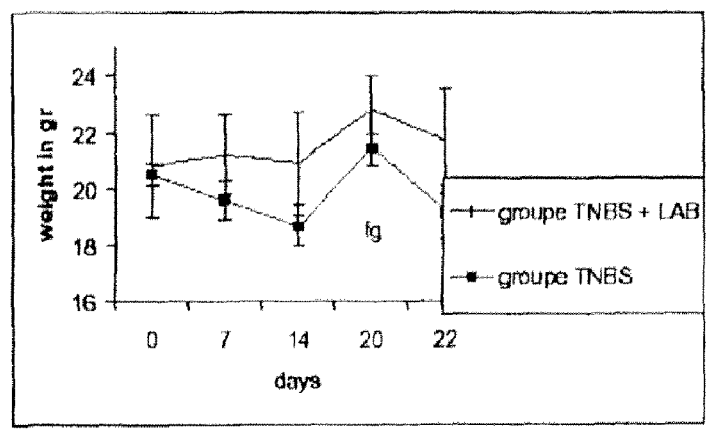
Figure 2: Wallace and Ameho scores, and weight evolution

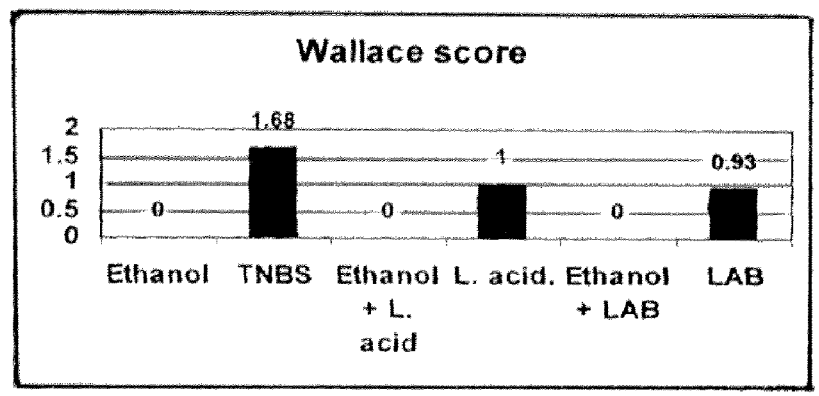
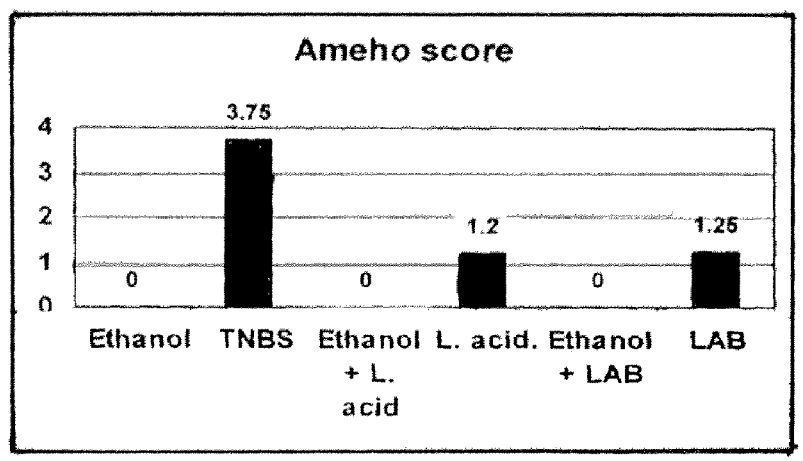
Figure 4: Wallace and Ameho scores
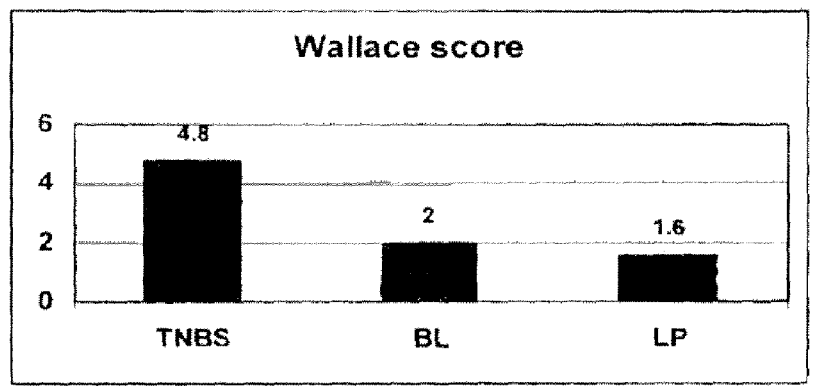
Figure 6: Wallace scores

BACTERIAL COMPOSITION AND ITS USE

This application claims the priority benefit of U.S. application Ser. No. 11/594,543, filed Nov. 8, 2006, the disclosure of which is incorporated herein by reference, which claims the benefit of U.S. application Ser. No. 10/310,549, filed Dec. 5, 2002.

The subject of the present invention is a bacterial composition, an immunomodulation method and the use of this composition. Immunomodulation is the capacity to improve the global immune functions either in healthy or in pathologic situations.

Among bacteria, some have a positive influence on the immune system of the intestinal medium, in particular lactic acid bacteria and bifidobacteria, and are termed "probiotic" bacteria or strains.

The expression probiotic bacteria or strains is understood to mean a strain which, when ingested live, exerts a beneficial effect on the host by having an action on the balance of the intestinal flora. These probiotic strains have the capacity to survive following passage across the upper part of the digestive tube. They are non-pathogenic, non-toxic and exert a beneficial action on health through in one hand their ecological interactions with the resident flora of the digestive tract and in the other hand their ability to positively influence immune system, through their effects onto the GALT (gut associated immune tissue). According to the probiotic definition, those bacteria when given in sufficient numbers have the capacity to transit alive all along the gut. There they become part of the resident flora or the period of administration. The so called colonization (or transient colonization) allow the probiotic bacteria to exert beneficial effect, such as repression of potentially pathogen micro-organisms on the flora and interactions with the gut immune system.

The probiotic strains most widely used, in particular in dairy products, are mainly bacteria and yeasts, of the following genera *Lactobacillus* spp, *Streptococcus* spp, *Enterococcus* spp and *Bifidobacterium* spp and *Sacharomyces* spp. Among the probiotic effects reported for those bacteria, one can cite for example, improvement of lactose tolerance, prevention and or treatment of gastrointestinal and urogenital infections, reduction of some cancers, decrease of blood cholesterol. However, it should be highlighted that not all the individual strains from the genera described above have those effects, but only some carefully selected strains do.

Thus in order to satisfy the requirements for performant probiotic strains, it has become necessary to select strains or a mixture thereof which is efficient and which allow stimulation of the immune system (immunomodulation).

Accordingly, the problem which the present invention proposes to solve is to provide a bacterial composition having probiotic properties.

The aim of the present invention is to satisfy these requirements.

For this purpose, the present invention provides a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

Another subject of the invention is an immunomodulation method.

The subject of the invention is also a food or pharmaceutical composition comprising the bacterial compositions described above.

Another subject of the invention is also the use of this composition in the preparation of a carrier administered to humans or to animals for a therapeutic or prophylactic purpose in the gastrointestinal system.

The composition of the invention has the advantage of providing unquestionable virtues which enrich the range of available strains.

Such a composition is particularly advantageous when it is administered to humans or to animals for a therapeutic or prophylactic purpose in the gastrointestinal system, in particular in the reduction of inflammatory and/or allergic reactions.

The advantage of the present invention is also to preserve all its properties when it is incorporated into a pharmaceutically acceptable carrier or into a food product.

Other advantages and characteristics of the present invention will emerge more clearly on reading the description and the examples given purely by way of illustration and without limitation, which follow.

First of all, the subject of the invention is a bacterial composition having immunomodulation properties comprising at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

The *Lactobacillus acidophilus* used according to the invention is a Gram-positive strain. Advantageously, it is a catalase-negative strain, with a homofermentative metabolism giving rise to the production of lactic acid.

The *Lactobacillus acidophilus* used according to the invention may also produce a bacteriocin, lactucin, which is active against other microorganisms.

Preferably, it is a *Lactobacillus acidophilus* exhibiting good resistance to pepsin, under acidic pH conditions (about at least 73% of the bacteria are still alive after 40 minutes of treatment).

More particularly, the *Lactobacillus acidophilus* used according to the invention exhibits a very good resistance to pancreatin (at least 100% of the bacteria are still alive after 40 minutes of treatment).

Advantageously, the *Lactobacillus acidophilus* used according to the invention exhibits good tolerance to bile salts.

Preferably, a *Lactobacillus acidophilus* described as being "hydrophobic", that is to say which exhibits a high affinity for hydrophobic organic solvents, polar or not polar, such as for example n-decane, chloroform, hexadecane or xylene, will be used.

The *Lactobacillus acidophilus* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), $\gamma$-interferon ($\gamma$-IFN) and tumour necrosis factor $\alpha$ (TNF$\alpha$). On the other hand, the *Lactobacillus acidophilus* used according to the invention induces little or no secretion of interleukins 12 (IL12) using this same test.

The *Lactobacillus acidophilus* used according to the invention is *Lactobacillus acidophilus* PTA-4797. This *Lactobacillus acidophilus* strain was deposited according to the Treaty of Budapest at the American Type Culture Collection where it is recorded under the deposit number PTA-4797.

One embodiment of the composition according to the invention is a bacterial composition comprising *Lactobacillus acidophilus* PTA-4797.

The composition made of probiotic bacteria according to the invention may also comprise at least one *Lactobacillus plantarum* strain.

The *Lactobacillus plantarum* strain used according the invention is preferably a Gram-positive strain. Advantageously, it is a catalase-negative strain, with a homofermentative metabolism giving rise to the production of lactic acid.

Preferably, it is a *Lactobacillus plantarum* which is resistant to pepsin under acidic pH conditions (about at least 95% of the bacteria are still alive after 40 minutes of treatment).

More particularly, the *Lactobacillus plantarum* used according to the invention exhibits good resistance to pancreatin (about at least 79% of the bacteria are still alive after 40 minutes of treatment).

Advantageously, the *Lactobacillus plantarum* used according to the invention exhibits good resistance to bile salts.

The *Lactobacillus plantarum* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), γ-interferon (γ-IFN) and tumour necrosis factor α (TNFα). On the other hand, the *Lactobacillus plantarum* used according to the invention induces little or no secretion of interleukins 12 (IL12) using this same test.

The *Lactobacillus plantarum* used according to the invention is *Lactobacillus plantarum* PTA-4799. This *Lactobacillus plantarum* strain was deposited according to the Treaty of Budapest at the American Type Culture Collection where it is recorded under the deposit number PTA-4799.

One embodiment of the composition according to the invention is a bacterial composition comprising *Lactobacillus plantarum* PTA-4799.

The composition made of probiotic bacteria according to the invention may also comprise at least one *Lactobacillus salivarius* strain.

The *Lactobacillus salivarius* strain used according to the invention is a Gram-positive strain. Advantageously, it is a catalase-negative strain, with a homofermentative metabolism giving rise to the production of lactic acid.

More particularly, the *Lactobacillus salivarius* used according to the invention exhibits good resistance to pancreatin (at least 100% of the bacteria are still alive after 40 minutes of treatment).

The *Lactobacillus salivarius* used according to the invention can induce the secretion of cytokines. This detection of the induction of cytokines was made by means of a test for in vitro stimulation of isolated peripheral blood mononuclear cells (PBMC). Among the cytokines induced during this test, there may be mentioned interleukins 10 (IL10) and tumour necrosis factor α (TNFα). On the other hand, the *Lactobacillus salivarius* used according to the invention induces little or no secretion of interleukin 12 (IL12) and γ-interferon (γ-IFN) using this same test.

The *Lactobacillus salivaris* used according to the invention is *Lactobacillus salivarius* PTA-4800. This *Lactobacillus salivarius* strain was deposited according to the Treaty of Budapest at the American Type Culture Collection where it is recorded under the deposit number PTA-4800.

One embodiment of the composition according to the invention is a bacterial composition comprising *Lactobacillus salivarius* PTA-4800.

The composition made of probiotic bacteria according to the invention may also comprise at least one *Lactobacillus paracasei* strain.

The *Lactobacillus paracasei* used according to the invention is a Gram-positive strain. Advantageously, it is a catalase-negative strain, with a homofermentative metabolism giving rise to the production of lactic acid.

Preferably, it is a *Lactobacillus paracasei* exhibiting poor resistance to pepsin, under acidic pH conditions (about at least 17.5% of the bacteria are still alive after 40 minutes of treatment).

More particularly, the *Lactobacillus paracasei* used according to the invention exhibits a very good resistance to pancreatin (about at least 100% of the bacteria are still alive after 40 minutes of treatment).

Advantageously, the *Lactobacillus paracasei* used according to the invention exhibits good tolerance to bile salts.

The *Lactobacillus paracasei* used according to the invention can induce the production of cytokines. This detection of the induction of cytokines was made by means of a test for in vitro stimulation of isolated peripheral blood mononuclear cells (PBMC). Among the cytokines induced during this test, there may be mentioned interleukins 10 (IL10), γ-interferon (γ-IFN) and tumour necrosis factor α (TNFα). On the other hand, the *Lactobacillus paracasei* used according to the invention induces little or no secretion of interleukins 12 (IL12) using this same test.

The *Lactobacillus paracasei* used according to the invention is *Lactobacillus paracasei* PTA-4798. This *Lactobacillus paracasei* strain was deposited according to the Treaty of Budapest at the American Type Culture Collection where it is recorded under the deposit number PTA-4798.

One embodiment of the composition according to the invention is a bacterial composition comprising *Lactobacillus paracasei* PTA-4798.

The composition made of probiotic bacteria according to the invention may also comprises at least one *Bifidobacterium bifidum* strain.

The *Bifidobacterium bifidum* strain used according to the invention is a Gram-positive strain. Advantageously, it is a catalase-negative strain, with a heterofermentative metabolism giving rise to the production of lactic acid and acetic acid.

The *Bifidobacterium bifidum* used according to the invention is *Bifidobacterium bifidum* PTA-4801. This *Bifidobacterium bifidum* strain was deposited according to the Treaty of Budapest at the American Type Culture Collection where it is recorded under the deposit number ATCC PTA-4801.

One embodiment of the composition according to the invention is a bacterial composition comprising *Bifidobacterium bifidum* PTA-4801.

The composition made of probiotic bacteria according to the invention may also comprises at least one *Bifidobacterium lactis* strain.

The *Bifidobacterium lactis* strain used according to the invention is a Gram-positive strain. Advantageously, it is a catalase-negative strain, with a heterofermentative metabolism giving rise to the production of lactic acid and acetic acid.

The *Bifidobacterium lactis* used according to the invention is *Bifidobacterium lactis* PTA-4802. This *Bifidobacterium lactis* strain was deposited according to the Treaty of Budapest at the American Type Culture Collection where it is recorded under the deposit number ATCC PTA-4801.

One embodiment of the composition according to the invention is a bacterial composition comprising *Bifidobacterium lactis* PTA-4801.

Another embodiment of the composition according to the invention is a bacterial composition comprising at least one strain selected from the group consisting of *Lactobacillus* acidophilus PTA-4797, *Lactobacillus plantarum* PTA-4799, and *Bifidobacterium lactis* PTA-4802.

More particularly, the composition according to the invention may comprise at least 2 strains selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

More particularly, the composition according to the invention may comprise 3 strains selected from the group consisting of *Lactobacillus acidophilus* PTA-4797, *Lactobacillus plantarum* PTA-4799, *Lactobacillus* salivarius PTA-4800, *Lactobacillus paracasei* PTA-4798, *Bifidobacterium bifidum* PTA-4801 and *Bifidobacterium lactis* PTA-4802.

Preferably, the composition according to the invention may comprise a blend of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium lactis* PTA-4802 and *Bifidobacterium bifidum* PTA-4801.

The composition according to the invention may be used in the form of a bacterial suspension, before or after freezing, or of a freeze-dried powder. Indeed, regardless of the form used, the composition may be frozen.

The relative proportion of each bacterium in the composition can vary in large limit for example from 1/99 to 99/1 in the case there is at least 2 strains.

The composition according to the invention may comprise from $10^6$ to $10^{11}$ CFU of bacteria/g of composition, and more particularly from $10^8$ to $10^{11}$ CFU of bacteria/g of composition. The term CFU means "colony forming units". The expression gram of composition is understood to mean the food product or pharmaceutical preparation, and preferably $10^9$ to $10^{11}$ CFU/g if in a freeze-dried form.

The composition according to the invention is useful for the treatment, the primary prevention or the recurrence, and also the prevention and/or the reduction of inflammatory bowel disease.

The bacterial composition according to the invention is also useful for maintaining the homeostasis of the immune system.

The bacterial composition according to the invention is also useful for the prevention and/or the reduction of allergenicity.

The bacterial composition according to the invention is also useful as immunoadjuvant.

An other subject of the invention is also an immunomodulation method comprising the step of using at least one strain selected from the group consisting of *Lactobacillus acidophilus* PTA-4797, *Lactobacillus plantarum* PTA-4799, *Lactobacillus salivarius* PTA-4800, *Lactobacillus paracasei* PTA-4798, *Bifidobacterium bifidum* PTA-4801 and *Bifidobacterium lactis* PTA-4802.

The composition according to the invention may be used in the form of a food product or pharmaceutical preparation.

The expression pharmaceutical preparation is understood to mean for example a preparation in the form of capsule or tablet.

The subject of the invention is also a food, dietary supplement or pharmaceutical composition comprising the bacterial composition described above.

Preferably, the food composition comprising the composition according to the invention is a food supplements, a beverage product or a milk base powder.

More particularly, the food composition comprising the composition according to the invention is a dairy product.

More preferably the food composition comprising the composition according to the invention is an infant formula.

The food or pharmaceutical composition according to the invention may have immunomodulation properties.

Another subject of the invention is also the use of this composition in the preparation of a carrier administered to humans or to animals for a therapeutic or prophylactic purpose in the gastrointestinal system.

The invention provides also a pharmaceutical composition comprising the bacterial composition described above useful for the prevention of inflamatory bowel disease.

The invention provides also a pharmaceutical composition comprising the bacterial composition described above useful for immunomodulation.

The FIGS. 1, 3 and 5 are schedules of injection.
The FIGS. 2, 4 and 6 are Wallace and Ameho scores, and weight of loss.

Concrete but nonlimiting examples of the invention will now be described.

EXAMPLES

1/ PBMC Test:

PBMC (Peripheral Blood Mononuclear Cells) are prepared by centrifugation from human blood, derived from known donors and is further purified on a Ficoli gradient. Cells are harvested, washed, (red blood cells removed) and counted.

Bacteria are prepared according to standard conditions and counted by plating on agarose medium according to proper dilutions ($10^{-7}$, $10^{-8}$, $10^{-9}$ in Ringer solution).

Cells are washed 3 times and suspended (et non dissolved) in PBS buffer. A verifier par Dominique PBMC cells are stimulated for 48 hours with the bacteria (allow negative control with Phosphate Buffer Saline solution (PBS)) under appropriate conditions of $CO_2$. Then the supernatant containing the cytokines is frozen at −20° C.

Cytokines expression levels are determined by ELISA tests (<<Enzyme linked immuno sorbent assay>>). ELISA plates are coated with anti-cytokine antibody (overnight procedure) and the antibody is blocked with a surfactant, the tween 80.

A proper standard is prepared for known concentrations of cytokines which will cover the detection range of 15.62 till 2000 pg/ml (incubate overnight). Perform the anti-cytokine detection and quantify with streptavidin reaction on substrate (10 mg dABTS/10 ml of citric acid buffer 0.1 M, pH4.35/20 µl H2O2).

Cytokines are either pro-inflammatory/Th1 (TNFα, IFNγ, IL12) or anti-inflammatory (IL10).

| Strains | IL-10 | IL-12 | IFN-γ | TNF-α |
| --- | --- | --- | --- | --- |
| *L. acidophilus* PTA-4797 | 309 | | 1970 | 27591 |
| *L. salivarius* PTA-4800 | 6881 | 31 | 1148 | 23509 |
| *L. paracasei* PTA-4798 | 300 | 31 | 921 | 14046 |

The values are pg/ml.

2/ Preparation of a Composition made of *Lactobacillus acidophillus* PTA-4797, *Lactobacillus plantarum* PTA-4799 and *Bifidobacterium lactis* PTA-4802:

A blend of 3 strains is prepared containing *Lactobacillus acidophilus* PTA-4797, *Lactobacillus plantarum* PTA-4799, et *Bifidobacterium lactis* PTA 4802. This blend is named LAB.

To show in vivo, the immuno modulation capacity of this blend according to the invention, animal test were performed aimed at decreasing the chemically induced gut inflammation of mice. Several models were set-up to mimic human inflammatory bowel diseases.

In the first model, injections of 1 mg/mice of TNBS (trinitrobenzene sulfonic acid, which is a colitis inducing agent) on days 0, 7 and 14, and 2 mg/mice of TNBS on day 20 (double dose) will evoke a chronic colitis. The schedule of injection is drawn on FIG. 1. The intake of bacteria (LAB) on days −4 to −1, 6, 9, and 19 will show macroscopic and histological effects, which are scored on day 22, according to standard scores (Wallace and Ameho respectively).

The results obtained (see FIG. 2) clearly showed an improvement of the colitis symptoms evidenced by
  reduction of the increase of the submucosa
  reduction of the inflammation
  less weight loss A second model of chronic colitis was also used (based on Camoglio et al., Eur J Immunol 2000), 2 mg/mice of TNBS injected by intra-rectal route on days 0, 7, and 14 induce a serious chronic colitis. The schedule of injection is drawn on FIG. 3. The intake of bacteria (LAB) on days −5 to −1, on days 5 and 12 (FIG. 3) will show macroscopic and histological effects, which are scored on day 16, according to standard scores (Wallace and Ameho respectively).

The results obtained clearly showed an improvement of the colitis symptoms evidenced (see FIG. 4), by
  absence of necrotic lesions
  reduction of the increase of the submucosa
  reduction of the inflammation A third acute model of mice colitis was also set up. 100 mg/kg mice of TNBS is injected on day 0. This will evoke an acute colitis. The schedule of injection is drawn on FIG. 5. The intake of *Bifidobacterium lactis* PTA-4802 or *Lactobacillus plantarum* PTA-4799 ($10^7$ bacteria/mouse) on days −5 to 0 show macroscopic and histological effects which are scored on day 2.

Clear macroscopic improvement of the colitis symptoms were evidenced for strains *Bifidobacterium lactis* PTA-4802 and *Lactobacillus plantarum* PTA-4799 (FIG. 6).

In general all the TNBS-induced colitis models in mice show that feeding LAB to these mice significantly reduced the level of intestinal translocation of indigenous bacteria from the intestinal flora into mesenteric lymph nodes and spleen after the induction of colitis. In addition, no translocation of probiotic bacterial strains according to the invention was observed.

3/ Resistance to Pepsin

The aim of this test is to evaluate the resistance of bacteria to the passage of the gastric barrier by determining the number of bacteria that survive after cultivation in the presence of a pepsin solution in acid environment. In short, 100 µl of a stock culture frozen at −80° C. is inoculated in 10 ml of MRS (Man Rogosa Sharp) culture medium and incubated overnight at 30° C. or 37° C. Then cells are washed 3 times in PBS at pH7 and the pellet is suspended in 1 ml PBS buffered and inoculated in 200 µl aliquots in 4 tubes with 1 ml of filtered pepsin solution at pH 2 supplemented with 300 µl of NaCl (0.5%). Cell count is performed on 100 µl aliquots taken from the tubes incubated at T0 (time of inoculation), T0+5 min; T020 min; T0+40 min; T0+60 min and dilutions are plated on MRS (100 µl) of $10^{-5}$ $10^{-6}$ et $10^{-7}$ (consecutive 10 fold dilutions made in 1 ml Ringer solution). The percentage surviving bacteria is calculated for each incubation time from the reading of the dilution series.

All results displayed in the tables are the result of triplicate experiments

| Strains | 5 min | 20 min | 40 min | 60 min |
|---|---|---|---|---|
| *L. acidophilus* PTA-4797 | 91 | 74 | 73 | 55 |
| *L. plantarum* PTA-4799 | 100 | 100 | 95 | 42 |
| *L. salivarius* PTA-4800 | 100 | 66 | 23 | 7 |
| *L. paracasei* PTA-4798 | 100 | 17.5 | 17.5 | 1.5 |

Results as % of survival compared to T=0.

4/ Resistance to Pancreatin

The aim of this test is to evaluate the resistance of bacteria to the passage of the intestinal transit by determining the number of bacteria that survive after cultivation in the presence of a pancreatin solution in basic environment. In short, 100 µl of a stock culture frozen at −80° C. is inoculated in 10 ml of MRS (Man Rogosa Sharp) culture medium and incubated overnight at 30° C. or 37° C. Cells are washed 3 times in PBS at pH7 and the pellet is suspended in 1 ml PBS buffered and inoculated in 200 µl aliquots in 4 tubes with 1 ml of filtered pancreatin solution at pH 8 supplemented with 300 µl of NaCl (0.5%). Cell count is performed on 100 µl aliquots taken from the tubes incubated at T0 (time of inoculation), T0+5 min; T0+20 min; T0+40 min; T0+60 min; T0+120 min and dilutions are plated on MRS (100 µl) of $10^{-5}$, $10^{-6}$, $10^{-7}$ (consecutive 10 fold dilutions made in 1 ml Ringer solution). The percentage surviving bacteria is calculated for each incubation time from the reading of the dilution series. All results displayed in the tables are the result of triplicate experiments.

| Strains | 5 min | 20 min | 40 min | 60 min | 120 min |
|---|---|---|---|---|---|
| *L. acidophilus* PTA-4797 | 83 | 100 | 100 | 170 | 170 |
| *L. salivarius* PTA-4800 | 100 | 115 | 152 | 158 | 155 |
| *L. plantarum* PTA-4799 | 86 | 72 | 79 | 84 | 87 |
| *L. paracasei* PTA-4798 | 65 | 100 | 100 | 100 | 100 |

Results as % of survival compare to T=0.

5/ Resistance to Bile Salts

The experimental is procedure is as follows. 100 µl culture of a stock frozen at −80° C. is inoculated in 10 ml de milieu de culture MRS (Man Rogosa Sharp) and incubated overnight at 30° C. or 37° C. The optical density (OD) is measured and a dilution is prepared (OD=0.05 to 0.1) in two bottles. One of the culture bottles is supplemented with a 0.3% solution of bile salts (750 µl of a filtered 12% solution) and incubated at the correct temperature. The OD is regularly measured until a OD of 0.3 is reached in the control bottle without bile salts. At that point the OD of the supplemented bottle is measured and one starts to measure the time needed to obtain the same OD of 0.3. The resistance of the strain is therefore evaluated as the delay in growth time.

Results are coded as sensitive (0; more than 60 minutes), tolerant (1; between 15 and 60 minutes) or resistant (2; less than 15 minutes).

All results displayed in the tables are the result triplicate experiments

| Strains | Resistance |
|---|---|
| L. acidophilus PTA-4797 | 1 |
| L. plantarum PTA-4799 | 2 |
| L. paracasei PTA-4798 | 2 |

6/ Hydrophobicity and Affinity for Organic Solvents

The MATS test as described by Rosdenberg et al., 1980 (FEMS Microbiol. Letters 9; 29-33) has been used. In short the test measures (grown overnight under normal in vitro growth conditions and washed twice in PBS) the hydrophobicity and polarity of the bacterial cell wall, based on the repartition (measured by optical density) of the bacteria into two non mixable liquid aqueous phases and five respective solvents. Growth medium is MRS (Man Rogosa Sharp) and the aqueous phase is a buffer as PBS. The solvents were decane, hexadecane, ethyl acetate, chloroform and xylene.

The affinity for chloroform, acid solvent, reflects the electron donor nature of the bacterium (basic reaction)

The affinity for Ethyl Acetate, basic solvent, reflects the electron acceptor nature of the bacterium (acid reaction)

The affinity for apolar solvents (decane, hexadecane, xylene) reflects the hydrophobic character of the bacterium.

Possibly a high hydrophobicity is related to the presence of glycoproteins on the cell wall surface, while a low hydrophobicity could be linked to the presence of polysaccharides on the cell wall surface.

% D'HYDROPHOBICITY=$(1-A/A0) \times 100$ with

AO: Original OD at 540 nm (set more or less at OD=0.6 in PBS)

A: Optical density of ageous phase (for 1 ml) after vortexing and stabilisation period

| Strains | Decane | Hexadecane | Ethyl acetate | Chloroform | Xylene |
|---|---|---|---|---|---|
| L. acidophilus PTA-4797 | 81.9 | 60.4 | 44.2 | 90.3 | 90.9 |
| L. salivarius PTA-4800 | 23.02 | 38.17 | 2.25 | 79.28 | 51.18 |
| L. paracasei PTA-4798 | 36.5 | 37.4 | 28.8 | 45.2 | 30.6 |
| L. plantarum PTA-4799 | 25.3 | 25.6 | 28.7 | 28.8 | 21.9 |

The invention claimed is:

1. A method for modulating the immune system of a human or animal in need thereof, said method comprising the step of administering to said human or animal in need thereof an effective amount of a bacterial composition comprising *Lactobacillus paracasei* PTA-4798.

2. The method according to claim 1, wherein said method is a method for stimulating the immune system of a human or an animal in need thereof.

3. The method according to claim 1, wherein said bacterial composition further comprises at least one additional strain selected from the group consisting of *Lactobacillus acidophilus* PTA-4797, *Lactobacillus plantarum* PTA-4799, *Bifidobacterium bifidum* PTA-4801.

4. The method according to claim 1, wherein said bacterial composition further comprises at least two additional strains selected from the group consisting of *Lactobacillus acidophilus* PTA-4797, *Lactobacillus plantarum* PTA-4799, *Bifidobacterium bifidum* PTA-4801.

5. The method according to claim 1, wherein said bacterial composition comprises a blend of *Lacrobacillus paracasei* PTA-4798, *Lactobacillus acidophilus* PTA-4797, *Lactobacillus plantarum* PTA-4799, *Bifidobacterium bifidum* PTA-4801.

6. The method according to claim 1, wherein said bacterial composition comprises from $10^6$ to $10^{11}$ CFU of bacteria/g of composition.

7. The method according to claim 1, wherein said bacterial composition comprises from $10^8$ to $10^{11}$ CFU of bacteria/g of composition.

* * * * *

UNITED STATES PATENT AND TRADEMARK OFFICE
CERTIFICATE OF CORRECTION

PATENT NO. : 8,071,086 B2  
APPLICATION NO. : 12/778509  
DATED : December 6, 2011  
INVENTOR(S) : Dennin et al.

Page 1 of 1

It is certified that error appears in the above-identified patent and that said Letters Patent is hereby corrected as shown below:

Title Page, please insert the following as item (60) under the heading "Related US Application Data":

--Divisional of application No. 11/594,543, filed Nov. 8, 2006, now Pat. No. 7,740,838, which is a divisional of application No. 10/310,549, filed Dec. 5, 2002, now Pat. No. 7,179,460.--

Signed and Sealed this  
Sixth Day of August, 2013

Teresa Stanek Rea  
*Acting Director of the United States Patent and Trademark Office*